United States Patent [19]

Mosebach et al.

[11] Patent Number: 5,047,014
[45] Date of Patent: Sep. 10, 1991

[54] MEDICAL PUMP DEVICE

[75] Inventors: Wolfgang Mosebach, Dagobertshausen; Rolf Heitmeier, Baunatal; Reinhard Knuth, Melsungen, all of Fed. Rep. of Germany

[73] Assignee: B. Braun Melsungen AG, Melsungen, Fed. Rep. of Germany

[21] Appl. No.: 496,342

[22] Filed: Mar. 20, 1990

[30] Foreign Application Priority Data

Apr. 15, 1989 [DE] Fed. Rep. of Germany ....... 3912405

[51] Int. Cl.⁵ .............................................. A61M 31/00
[52] U.S. Cl. .............................. 604/67; 128/DIG. 13
[58] Field of Search ........... 604/65, 67, 153, DIG. 12, 604/DIG. 13

[56] References Cited

U.S. PATENT DOCUMENTS

| 4,185,851 | 1/1980 | Casson et al. | |
| 4,597,754 | 7/1986 | Thill et al. | 604/153 |
| 4,617,014 | 10/1986 | Cannon et al. | 604/67 |
| 4,652,260 | 3/1987 | Fenton, Jr. et al. | 604/67 |
| 4,671,792 | 6/1987 | Borsani | |
| 4,775,368 | 10/1988 | Iwatschenko | 604/65 |
| 4,838,857 | 6/1989 | Strowe et al. | 604/67 |
| 4,878,896 | 11/1989 | Garrison et al. | 604/65 |
| 4,945,279 | 7/1990 | Samiotes et al. | 604/67 |
| 4,978,335 | 12/1990 | Arthur, III | 604/67 |

FOREIGN PATENT DOCUMENTS 0078645 of 0000 .

Primary Examiner—Paul J. Hirsch
Attorney, Agent, or Firm—Spensley Horn Jubas & Lubitz

[57] ABSTRACT

A medical pump device having a hose pump and a replaceable pump hose and provided with a reading means that reads a code mounted on the pump hose. The code corresponds to the deviation of the delivery volume of the individual hose from the set delivery volume. In dependence on the coding signals, the control signals for the pump drive are corrected so that defined delivery rates are obtained even with in wide hose tolerances.

7 Claims, 2 Drawing Sheets

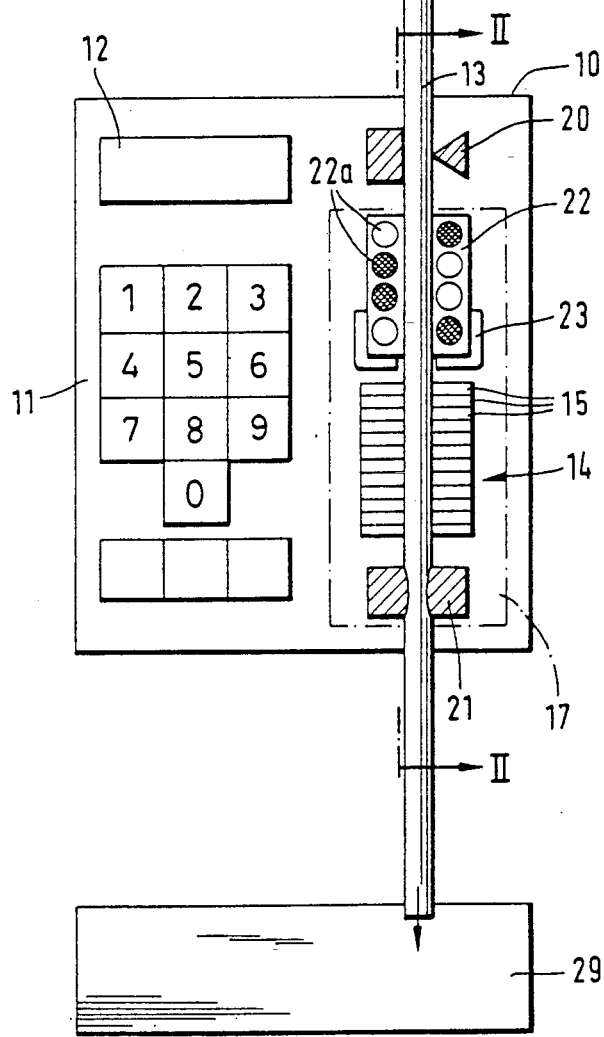
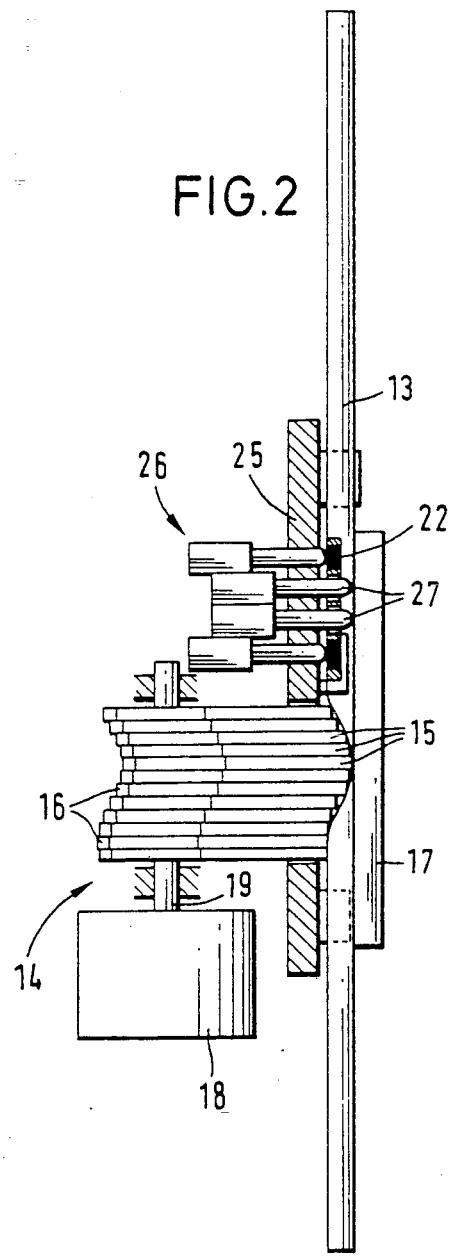

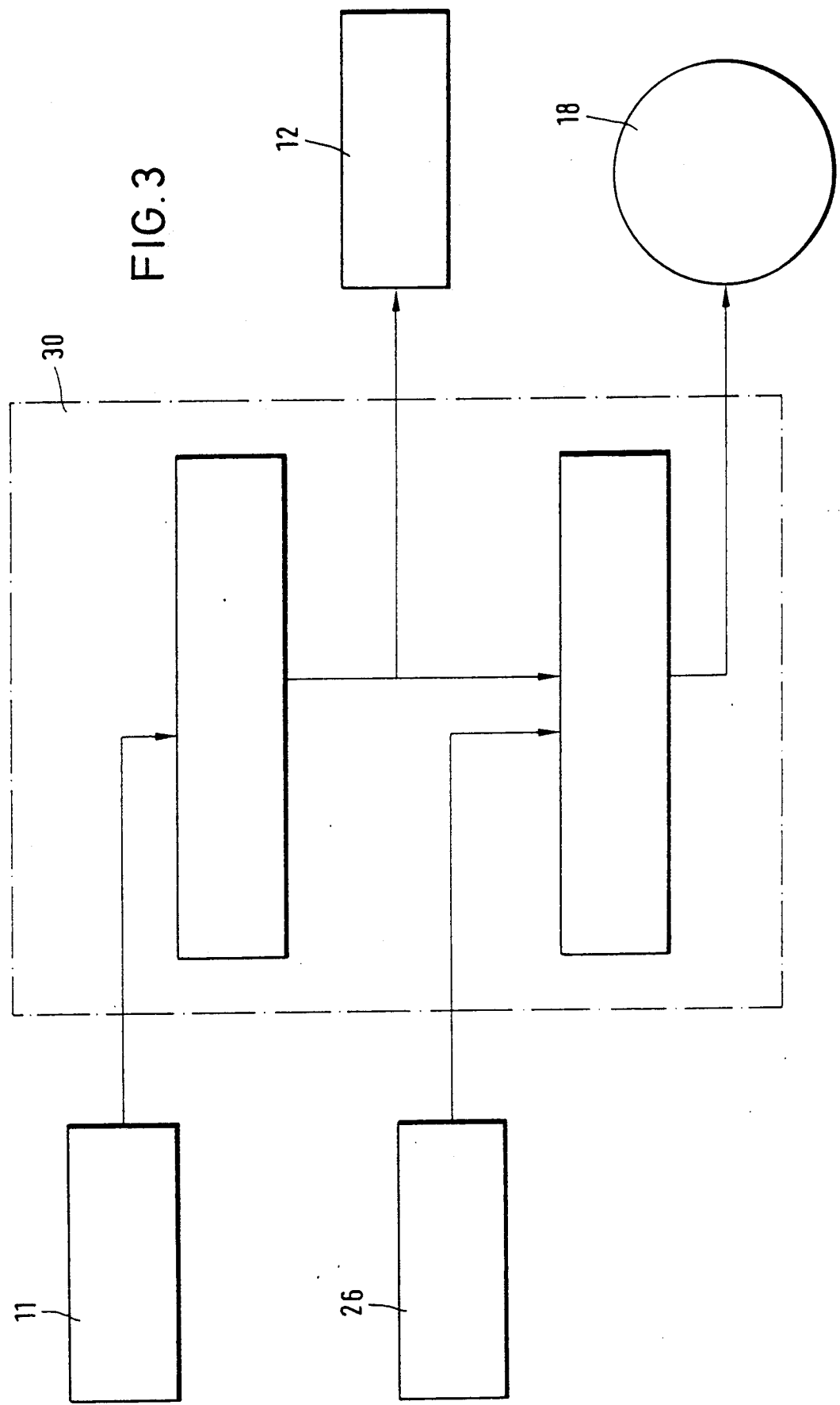

MEDICAL PUMP DEVICE

BACKGROUND OF THE INVENTION

1. Field of the Invention

The present invention relates to a medical pump device.

2. Description of Related Art

In the field of medicine, medical pump devices are used for introducing an exactly dosed rate of an infusion liquid into the body of a patient. Because of the high sterility requirements, medical pump devices uses hose pumps in which the liquid is advanced by repeatedly squeezing a pump hose. The pump hose is a one-way hose that is thrown away after use. Therefore, its production costs should be as low as possible. The same is true for other pump devices, e.g. blood pumps that draw blood from a patient's body or supply blood thereto. Also in this case, it is most important to obtain and maintain a desired rate of delivery.

The rate of delivery of a hose pump depends largely on the accuracy of the size of the pump hose. Prior to the present invention, particular importance was attributed to the production of a pump hose having a high degree of accuracy with respect to size, so as to exactly obtain a desired delivery rate. If the delivery volume of such pump hose lay beyond certain tolerance limits, the pump hoses were sorted out as waste. However, within the tolerance limits, the pump hoses used still have considerable deviations in the delivery volume. If narrow tolerances are chosen, a lot of waste is produced. If wide tolerances are chosen, large deviations of the delivery rate from the set delivery rate will occur.

It is an object of the present invention to provide a medical pump device in which an exact observation of the desired delivery rate is obtained without any particular requirements as to the accuracy of the size of the pump hose.

SUMMARY OF THE INVENTION

In accordance with the present invention, this and other objectives are achieved by providing a pump device in which the individual pump hoses are respectively provided with a coding that represents a measure of the individual delivery volume of that hose or the deviations form the set delivery volume. In this way, each hose is provided with information on its individual delivery volume. This information is read by a reading device of the pump device. The control signals that determine the drive speed of the hose pump are corrected by the read code signals, so that the actual drive speed of the pump is adjusted to the hose used such that the actual delivery rate corresponds to the predetermined delivery rate with a high degree of accuracy, independent of the deviation of the delivery volume of the pump hose concerned from the set delivery volume.

The coding may be provided on a coding carrier attached to the hose or on the hose itself, e.g. in the form of machine readable rings or other markers.

According to an advantageous embodiment of the invention, the hose has a fixing device that allows the hose to be fixed at the housing of the pump device only in a defined position. In this defined position, the coding is sensed by the reading means. The reading of the coding is done automatically after the hose has been inserted into the housing and prior to the starting of the pump. The operator need not take any particular measures and the reading of the correction code into the reading means cannot be forgotten.

The invention is advantageously applicable in a microprocessor-controlled infusion device and only requires a corresponding programming of the microprocessor in order to effect the correction of the drive speed of the pump so that a certain delivery rate is obtained. However, the invention may also be used in other medical pump devices, such as microprocessor-controlled blood pumps, dialytic pumps and the like.

BRIEF DESCRIPTION OF THE DRAWINGS

A detailed description of a preferred embodiment of the invention will be made with reference to the accompanying drawings.

FIG. 1 shows a front view of an infusion device.

FIG. 2 shows a schematic illustration of a vertical section of an infusion device substantially along line II—II of FIG. 1.

FIG. 3 shows a block diagram of the control of an infusion device.

DETAILED DESCRIPTION OF THE PREFERRED EMBODIMENTS

The following detailed description is of the best presently contemplated mode of carrying out the invention. This description is not to be taken in a limiting sense, but is made merely for the purpose of illustrating the general principles of the invention. The scope of the invention is best defined by the appended claims.

As illustrated in FIG. 1, the infusion device has a housing 10 provided with an input keyboard 11 for inputting the delivery rate and other data and a display means 12. A vertical channel is provided at the front side of the housing 10, in which vertical channel the pump hose 13 of the hose pump 14 may be inserted. In the illustrated embodiment, the hose pump 14 is a finger-type pump with numerous pump fingers 15 driven by cams 16 that sit on a common drive shaft 19. The drive shaft 19 is driven by a motor and the cams 16 are provided such that they periodically move the pump fingers 15 transversely to the pump hose 13. All pump fingers 15 are in different phases of their linear movement so that the squeezing of the hose 13 effected by the pump fingers moves linearly in the direction of the hose. The hose 13 is supported by a plate-shaped abutment 17 that is arranged before the housing 10 in the manner of a door.

The hose 13 extends in the vertical channel provided in the front wall of the housing 10 and covered by the abutment 17 over a part of its length. A safety clamp 20 is arranged above the pump 14 may be operated to seal the hose 13. A pressure sensor 21 for measuring the internal pressure of the hose 13 is arranged below the hose pump 14.

A coding plate 22 carrying the coding 22a is attached to the hose 13. In the illustrated embodiment, the coding consists of punched and non-punched holes or portions of the coding plate 22. The coding plate 22 has two wings extending on opposite sides of the hose 13 which carry the coding 22a adjacent to the hose 13. In the illustrated example there are two vertical columns having four coding positions each, so that a total of $2^8 = 256$ different code words can be realized.

Further, the housing 10 is provided with a fixing device 23 that insures that the hose 13 may be inserted in a defined position only and that, in doing so, the coding plate 22 also is in a defined position. In the present embodiment, the fixing device 23 consists of two L-shaped brackets between which the hose 13 passes and which form bearings and lateral supports for the coding plate 22. The coding plate 22 simultaneously forms a suspension means for suspending the house 13 at the housing. The plate-shaped abutment 17 that supports the hose 13 against the force of the pump fingers 15 extends upward beyond the area of the coding plate 22 so that the coding plate is covered by the abutment 17. This insures that the coding plate 22 will lie against the housing wall 25 forming the bottom of the hose channel when the abutment 17 is closed.

The reading means 26 is mounted on the housing wall 25. The reading means 26 has a sensor 27 for each coding position, which in the illustrated embodiment is a mechanical sensor pin. All sensors 27 are biased towards the coding plate 22. If a coding position is a hole, the respective sensor 27 will penetrate the hole. If the coding position is closed, however, the sensor will hit this coding position. Coding signals are generated in dependence on the sensor positions, every coding signal consisting of a bit number corresponding to the number of coding positions.

After the production of the pump hose 13, the delivery volume of that hose is determined, e.g. by measuring the amount of liquid the hose can hold. If the actual delivery volume of the hose differs from the set delivery volume, a corresponding coding is provided on the coding plate 22, indicating the amount of the deviation. The coding which is provided if the delivery volume of the hose equals the set delivery volume has the value "0". Deviations of the delivery volume from the set delivery volume are coded corresponding to their amount, with the large number of coding steps or words allowing for very subtle degrees. With the coding provided, the hose is packed germ-free and delivered. For use, the hose is attached to the infusion device as described above, and its upper end is connected to an infusion solution container 28 from which the liquid is to be delivered to the patient 29.

The value of the delivery rate, manually set at the keyboard 11, is processed by the microprocessor 30, as shown in FIG. 3, and converted into control signals for the drive 18. In the microprocessor, a display correction of the input value is effected first. The value thus obtained is displayed at the display means 12 as the set delivery rate. Further, the correction value represented by the coding is supplied to the microprocessor which corrects the control signals supplied to the drive 18 such that the individual hose tolerances of the hose concerned are taken into account and the actual delivery rate corresponds to the displayed set delivery rate.

The presently disclosed embodiment is to be considered in all respects as illustrative and not restrictive, the scope of the invention being indicated by the appended claims, rather that the foregoing description, and all changes which come within the meaning and range of equivalency of the claims are therefore intended to be embraced therein.

What is claimed is:

1. A medical pump device comprising:
    a hose having a delivery volume,
    a hose pump having a drive controlled by signals in dependence on a set delivery rate,
    a housing configured to receive the hose,
    a coding associated with the hose, the coding containing information about the delivery volume of the hose,
    reading means for reading the coding associated with the hose, and
    control means in communication with the reading means for controlling the drive in response to the coding associated with the hose.

2. The medical pump device according to claim 1, comprising:
    fixing means for attaching the hose to the housing in a defined position, whereby the coding is detectable by the reading means.

3. The medical pump device according to claim 1, further comprising an abutment covering a portion of the hose, wherein the hose pump includes a plurality of pump fingers for squeezing the hose against the abutment, and wherein the reading means is arranged on the housing at a position at which the hose is not squeezed against the abutment by the pump fingers.

4. The medical pump device according to claim 1, wherein the coding is provided on a plate attached to the hose, and wherein the plate is disposed to lie against a wall of the housing when the hose is received by the housing.

5. A medical pump device according to claim 1, wherein the coding comprises a binary code.

6. A method of controlling the rate of delivery of fluid pumped through a hose having a delivery volume by a medical pump device, the method comprising:
    providing the hose with a code containing information about the delivery volume of the hose,
    reading the code provided with the hose, and
    controlling the medical pump device in response to the code provided with the hose,
    whereby the rate of delivery of fluid pumped through the hose is adjusted in accordance with the delivery volume of the hose to correspond to a predetermined rate of delivery.

7. An apparatus for controlling the rate of delivery of fluid pumped through a hose having a delivery volume by a medical pump device, the apparatus comprising:
    means for providing the hose with a code containing information about the delivery volume of the hose,
    means for reading the code provided with the hose, and
    means for controlling the medical pump device in response to the code provided with the hose,
    whereby the rate of delivery of fluid pumped through the hose is adjusted in accordance with the delivery volume of the hose to correspond to a predetermined rate of delivery.

* * * * *